(12) United States Patent
Quick

(10) Patent No.: US 6,267,759 B1
(45) Date of Patent: *Jul. 31, 2001

(54) SHAPED SCALPEL

(75) Inventor: Richard L. Quick, Trabuco Canyon, CA (US)

(73) Assignee: SenoRx, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/337,666

(22) Filed: Jun. 22, 1999

(51) Int. Cl.[7] ................................................. A61B 18/18
(52) U.S. Cl. .................................................. 606/47; 606/45
(58) Field of Search .......................... 606/39, 41, 45–48, 606/50, 170, 180

(56) References Cited

U.S. PATENT DOCUMENTS

| 3,955,578 | * | 5/1976 | Chamness et al. . | |
|---|---|---|---|---|
| 5,041,124 | | 8/1991 | Kensey . | |
| 5,437,665 | * | 8/1995 | Munro | 606/47 |
| 5,676,663 | | 10/1997 | Kim | 606/45 |
| 5,810,806 | | 9/1998 | Ritchart et al. . | |
| 5,951,550 | | 9/1999 | Shirley et al. | 606/45 |
| 6,036,681 | * | 3/2000 | Hooven | 604/506 |

FOREIGN PATENT DOCUMENTS

| 38048849 A1 | 9/1988 | (DE) . |
|---|---|---|
| WO 98/43531 | 10/1998 | (WO) . |

* cited by examiner

*Primary Examiner*—Linda C. M. Dvorak
*Assistant Examiner*—Roy Gibson
(74) *Attorney, Agent, or Firm*—Heller Ehrman White & McAuliffe LLP

(57) ABSTRACT

An electrosurgical tool includes a cutting loop, which can be an RF cutting loop, which is secured to a shaft which rotates about an axis which is perpendicular to the longitudinal axis of the tool.

20 Claims, 8 Drawing Sheets

SHAPED SCALPEL

BACKGROUND OF THE INVENTION

1. Field of the Invention

The present invention relates to handholdable surgical devices, and more particularly to shaped scalpels.

2. Brief Description of the Related Art

Surgical lesion removal has in the past been attempted using a variety of surgical tools and techniques, some of which are specially adapted for a particular procedure. For example, large lesion removal from, e.g., the human breast, is typically attempted through an open incision using an ordinary surgical knife or scalpel. While the use of scalpels is widely accepted, they are not designed to minimize the invasiveness of the procedure. During the procedure, it is usually necessary to form an incision which is much larger than the legion which is targeted for removal, so that the surgeon can work around, under, and over the legion to remove both the entire legion and a margin of tissue surrounding the lesion. The removal of a margin of tissue around the lesion is typically indicated, to be more certain that all of the lesion has been removed by the surgical procedure.

While the practice of removing tissue adjacent to a tissue mass of interest, e.g., a malignant or benign lesion, is followed in many lumpectomy procedures, the tools provided for a surgeon to remove the tissue are not well suited for performing the procedure. Straight and sculpted blade scalpels do not assist the surgeon in making the smallest cut necessary, and often require the surgeon to essentially dig out the tissue mass. The damage to the remaining tissues can be significant, resulting in considerable postoperative pain, excessive bleeding, long recovery times, the potential for infection, the potential for depression of the tissues at the surgical site (poor cosmesis) due to the removal of excessive tissue, and surface tissue scarring which is much larger than necessary.

SUMMARY OF THE INVENTION

According to a first exemplary embodiment of the present invention, a surgical tool comprises a handle having a proximal end, a distal end, and a movable actuator, a rigid probe attached to said handle distal end, a shaft rotatably mounted to said probe, a motion transmission member connecting said movable actuator and said shaft, a cutting wire secured to said shaft, and an electrical conductor in electrical communication with said cutting wire extending proximally through said probe.

According to a second exemplary embodiment of the present invention, a process of cutting tissue in a patient comprises the steps of supplying energy to a cutting wire which is secured to a rotatable shaft, and rotating the rotatable shaft.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DESCRIPTION OF THE PREFERRED EMBODIMENTS

Figure 1:
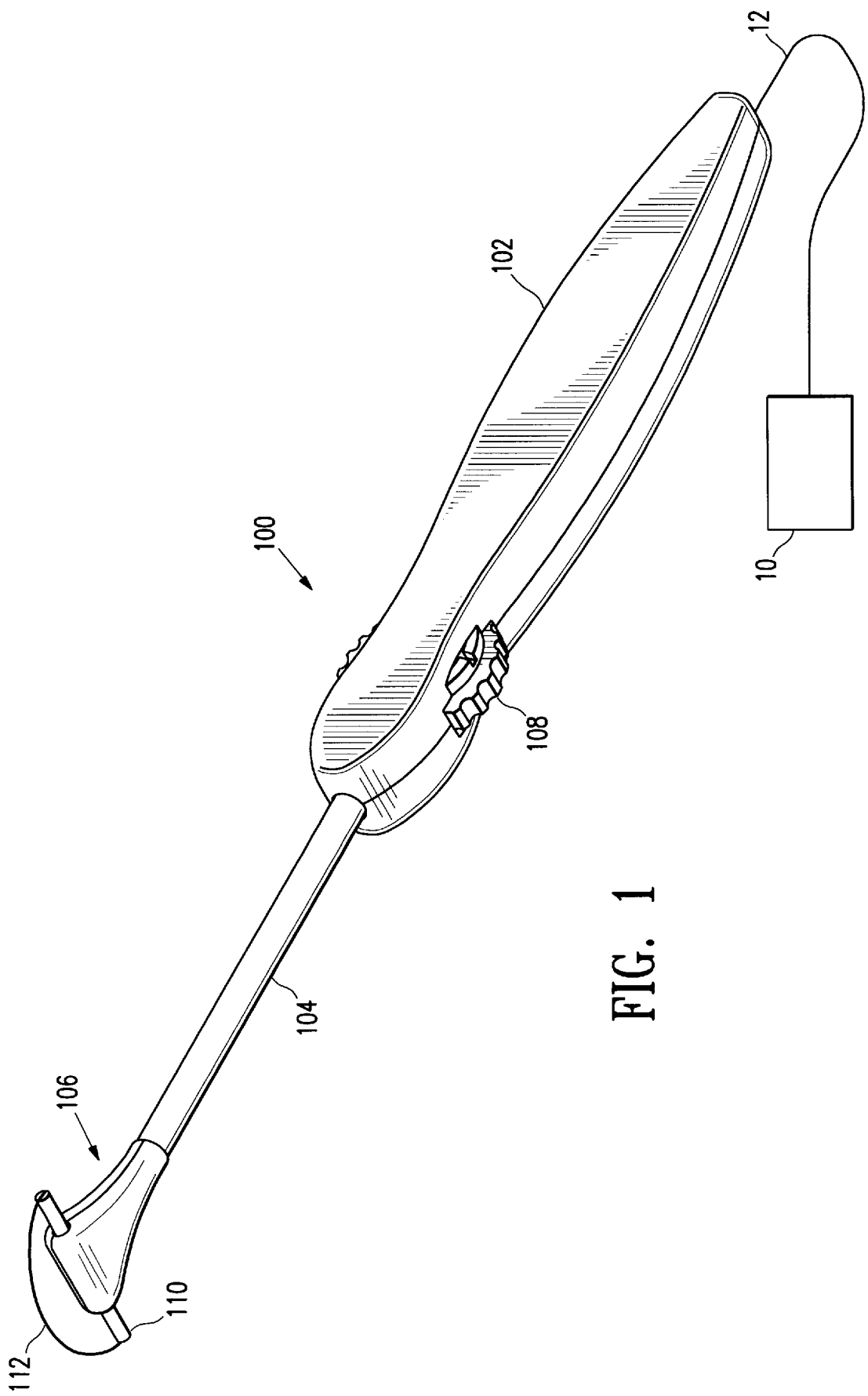
FIG. 1 is an illustration of a perspective view of a first embodiment of a surgical tool in accordance with the present invention.

Referring to the drawing figures, like reference numerals designate identical or corresponding elements throughout the several figures.

FIG. 1 illustrates a perspective view of a first exemplary embodiment of a surgical tool in accordance with the present invention. Shaped scalpel or tool 100 includes a handle 102 at a proximal end of the tool, and a relatively rigid, hollow probe 104 extending distally from the handle, and a cutting tip 106 at the distal end of the tool. Preferably, several of the components or elements of tool 100 are constructed of an electrically non-conductive (dielectric) material, while other components or elements are electrically conductive, for reasons explained in greater detail below.

Handle 102 includes a thumbwheel 108 which extends outside the housing, and which is rotatably mounted in or to the housing. Cutting tip 106 includes a transverse shaft 110 which is rotatably mounted in the cutting tip so as to be rotatable about the longitudinal axis of shaft 110, and a cutting wire 112 which is connected to shaft 110 and extends away from the distal end of the cutting tip. While the details of the operation of tool 100 will be described in greater detail below, a brief and general description of the tool will aid in an understanding of the tool. Tool 100 is connectable to a source of electrical energy 10 through an appropriate energy transmission line 12. Portions of tool 100 place source 10 in electrical communication with cutting wire 112. Thumbwheel 108 is operatively connected to rotatable shaft 110, so that rotation of the thumbwheel results in rotation of shaft 110 about the longitudinal axis of the shaft. As cutting wire is secured to rotatable shaft 110, rotation of the rotatable shaft, via rotation of thumbwheel 108, results in the cutting wire sweeping out a volume about the longitudinal axis of the rotatable shaft. When source 10 is placed in electrical communication with cutting wire 112, electrical energy is conducted to the cutting wire, which is then able to cut through tissue into which cutting tip 106 has been inserted. In accordance with a preferred embodiment of the present invention, source 10 is a source of radio frequency (RF) electrical energy, and cutting wire 112 is a monopolar RF cutting wire. As will be readily appreciated by one of ordinary skill in the art, a second pole (not illustrated) for conducting RF energy back is part of source 10. Less preferably, source 10 can be a source of low frequency or direct electrical current, for which cutting wire 112 is a resistive heating cutting wire. Other forms of energy and corresponding cutting wires will be readily appreciated by one of ordinary skill in the art, and are within the spirit and scope of the present invention.

Figure 2:
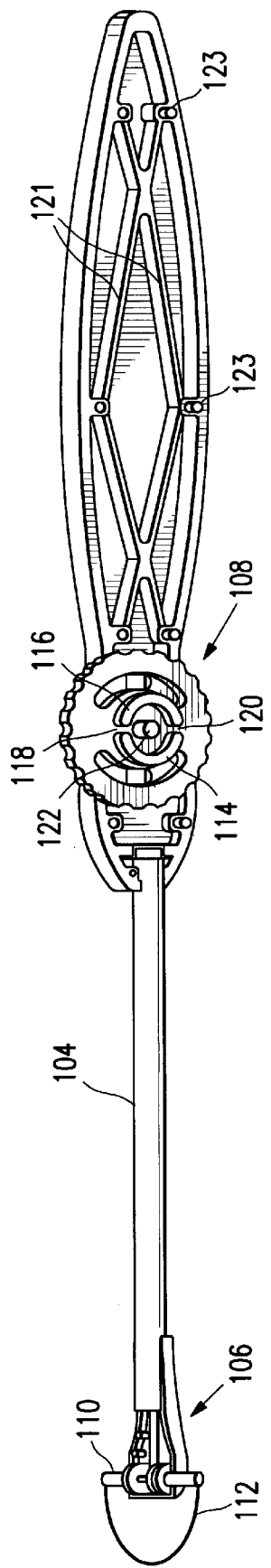
FIG. 2 is an illustration of the tool of FIG. 1, with portions broken away.

FIG. 2 illustrates the tool 100 of FIG. 1, with portions broken away to allow a better understanding of the features of tool 100. Thumbwheel 108 includes a pair of arcuate blocks 114, 116 which are separated by a pair of slots 118, 120. A post or pin 122 at the center of thumbwheel 108 is also provided. The purposes of arcuate blocks 114, 116, slots 118, 120, and post 122 will be described in greater detail below. Handle 102 also includes reinforcing ribs 121 and snap fit connection posts 123, for joining together two portions of the handle and reinforcing the handle, respectively, as will be readily appreciated by one of ordinary skill in the art.

Figure 3:
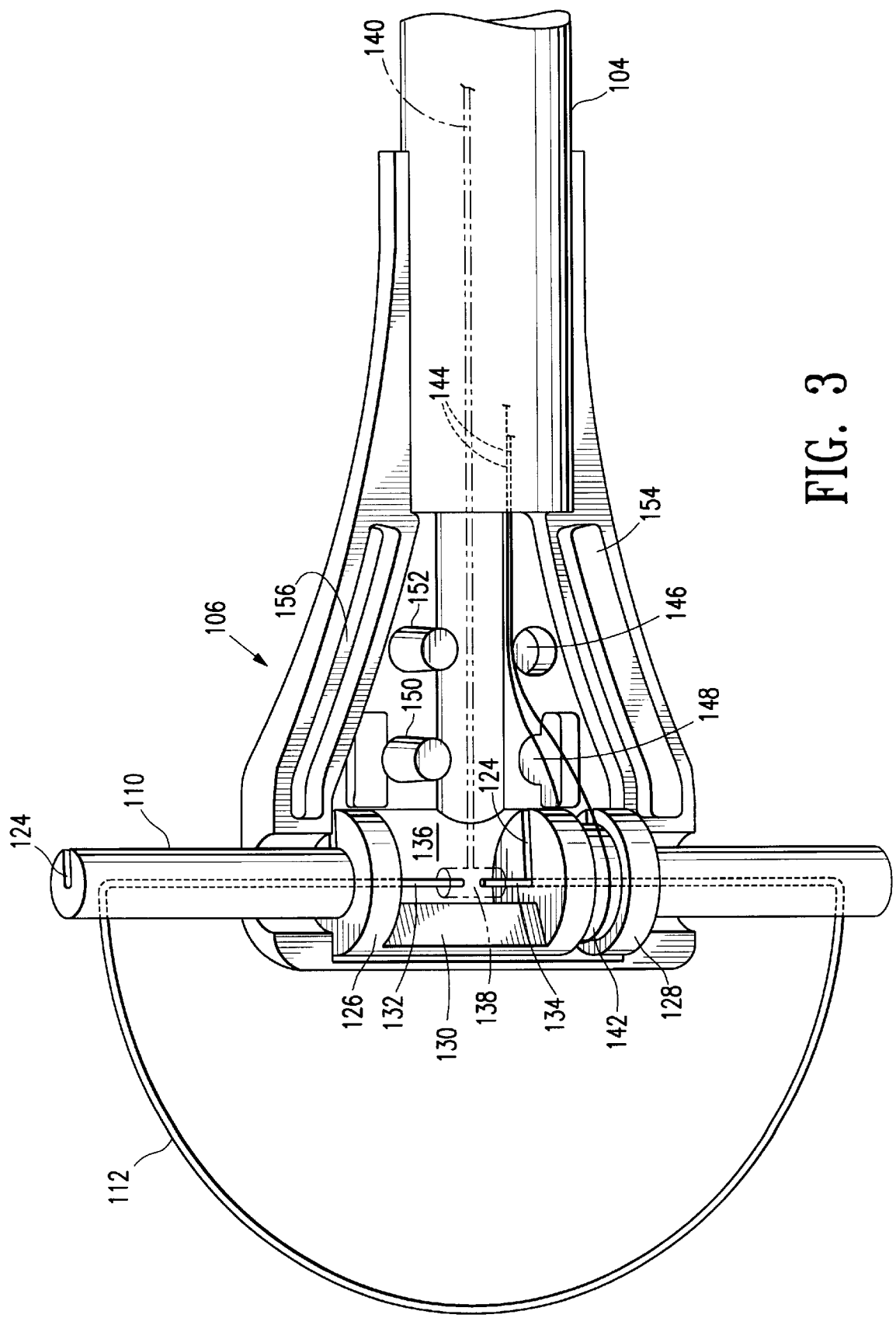
FIG. 3 is an illustration of a portion of the tool of FIGS. 1 and 2.

FIG. 3 is an illustration of a magnified view of distal portions of tool 100. Cutting wire 112 is mounted in or to rotatable shaft 110, and extends through the shaft to an open space 136. For this purpose, shaft 110 includes a longitudinally extending slot 124, through which cutting wire 112 is lead to form a loop. Shaft 110 also includes bearing supports 126, 128, which are positioned inside cutting tip 106 and together retain the shaft in the cutting tip. A connecting rib 130 extends between bearing supports 126, 128, and is preferably formed as a relatively narrow rib, to maximize space 136 between the bearing supports. Ends 132, 134 of cutting wire 112 extend into space 136.

An electrical connector 138, illustrated in phantom so as not to obscure the other structures within cutting tip 106, is connected to ends 132, 134, and to an electrical conductor 140, also illustrated in phantom. Conductor 140 extends proximally through probe 104, handle 102, and to source 10, as described above, and places cutting wire 112 in electrical communication with source 10.

Rotatable shaft 110 is connected to thumbwheel 108 so that rotation of the thumbwheel results in rotation of the rotatable shaft, as described above. The present invention is not limited to the particular structures illustrated in FIG. 3, as will be further discussed with reference to FIGS. 4–9, below. In FIG. 3, a circumferential channel 142 is formed in bearing 128 in which a push-and-pull wire 144 is looped. The two ends of wire 144 extend proximally to thumbwheel 108, through slots 118, 120, and are fixed to the thumbwheel using pins, knots, adhesive or the like. Thus, rotation of thumbwheel 108 causes one end of wire 144 to be pulled, causing the wire to rotate rotatable shaft 110 about its longitudinal axis, and therefore rotate cutting wire 112. To assist in rotating shaft 110, channel 142, wire 144, or both can be provided with structures which increase the friction between the wire and the shaft. Preferably, shaft 110 includes a transverse bore (not illustrated) in channel 142 through which wires 144 are pushed proximally and knotted, which fixes the wires to the shaft and allows the wires to rotate the shaft. Less preferably, yet still within the scope of the present invention, this can be accomplished by providing knurling in the channel, forming their engaging surfaces of materials which mutually bind to one another, providing a pinch roller which bears down into the channel and onto the wire, and other suitable expedients as will be readily apparent to one of ordinary skill in the art.

Cutting tip 106 is preferably formed of two housing shells which are joined together. Cutting tip 106 may include a block 154 and a slot 156 for mating with a pair of corresponding slots and block on the mating housing shell. The posts (not illustrated) which mate with recesses 146, 148, and which are similar to posts 150, 152, provide bearing surfaces for wire 144 to be directed toward channel 142, as suggested in FIG. 3.

Figure 4:
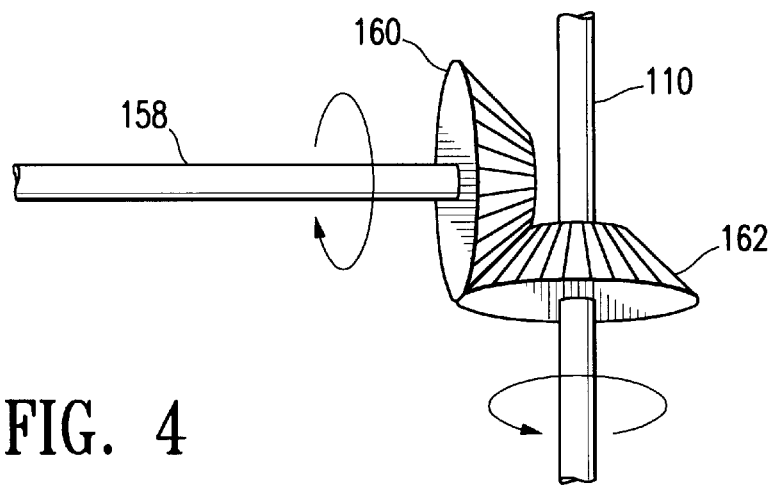
FIG. 4 is an illustration of a view of a second exemplary embodiment of first portions of a surgical tool in accordance with the present invention.
Figure 5:
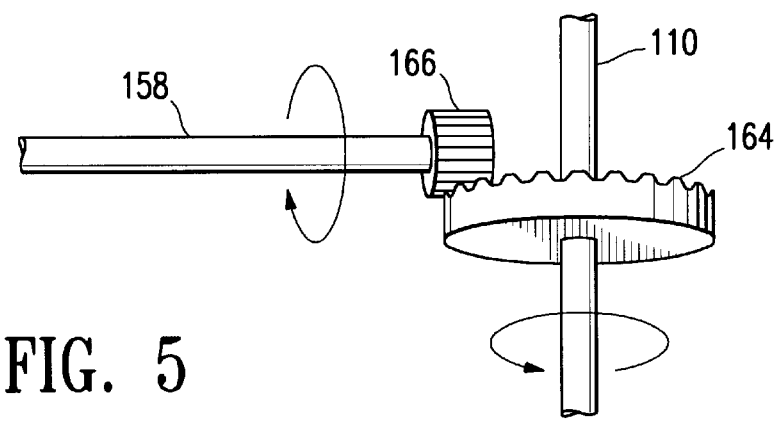
FIG. 5 is an illustration of a view of a third exemplary embodiment of first portions of a surgical tool in accordance with the present invention.
Figure 6:
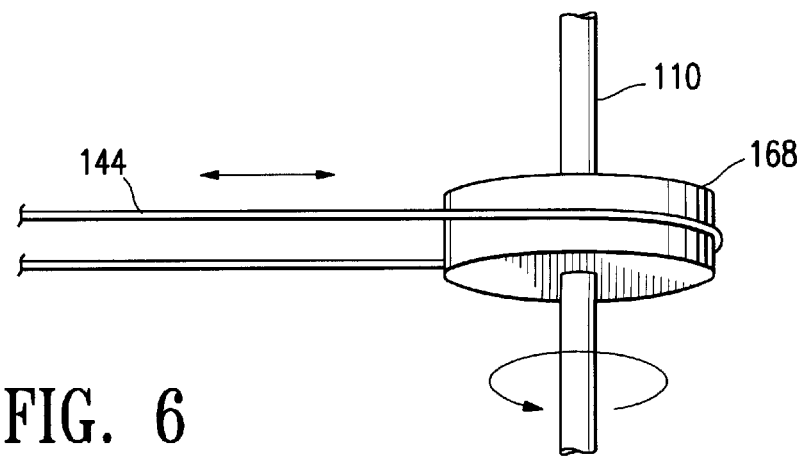
FIG. 6 is an illustration of a view of a fourth exemplary embodiment of first portions of a surgical tool in accordance with the present invention.
Figure 7:
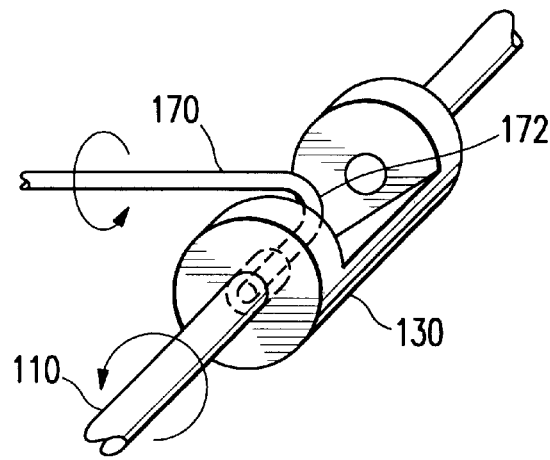
FIG. 7 is an illustration of a view of a fifth exemplary embodiment of first portions of a surgical tool in accordance with the present invention.
Figure 8:
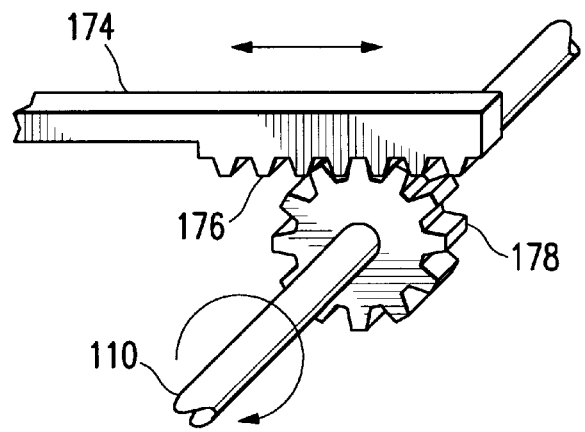
FIG. 8 is an illustration of a view of a sixth exemplary embodiment of first portions of a surgical tool in accordance with the present invention.
Figure 9:
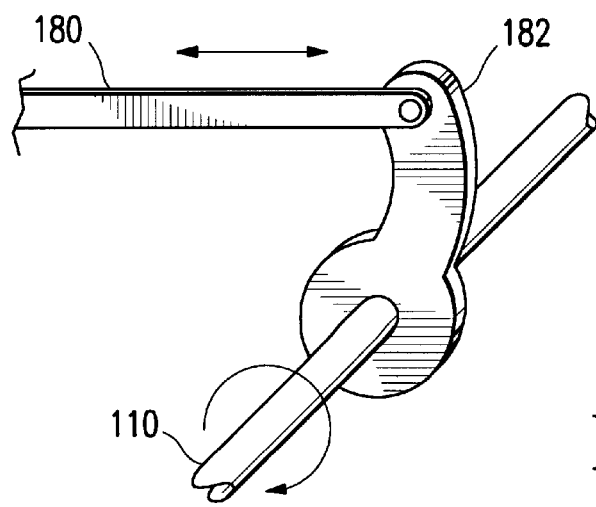
FIG. 9 is an illustration of a view of a seventh exemplary embodiment of first portions of a surgical tool in accordance with the present invention.

Turning now to FIGS. 4–9, numerous alternate embodiments of a mechanism in accordance with the present invention by which motion of thumbwheel 108, or a similar structure such as a sliding tab, lever, or the like, can be translated into rotation of rotatable shaft 110. As illustrated in FIG. 4, a rotatable shaft 158 can be provided with a beveled gear 160, which engages and drives a corresponding beveled gear 162 on shaft 110. Thus, rotation of shaft 158 is results in rotation of shaft 110. In the embodiment illustrated in FIG. 5, rotatable shaft 158 includes a pinion 166, which mates with a ring gear 164 of shaft 110. In the embodiment illustrated in FIG. 6, a push-and-pull wire 144 cooperates with a pulley 168 which is centered on shaft 110. In the embodiment illustrated in FIG. 7, a rotatable torque transmission cable 170 includes a hooked distal end 172 which is secured to shaft 110 so that the distal most end of cable 170 is coaxial with shaft 110. Rotation of cable 170 is transmitted through the cable to hooked distal end 172 which then rotates shaft 110. In the embodiment illustrated in FIG. 8, a rack 174 is slidable along the length of probe 104 (see FIGS. 1–3), and includes teeth 176 at the distal end of the rack. A pinion gear 178 is attached to shaft 110, so that longitudinal motion of rack 174 results in rotation of shaft 110. In the embodiment illustrated in FIG. 9, a relatively rigid push rod 180 is rotatably connected to a lever 182 on shaft 110; longitudinal movement of pushrod 180 causes lever 182 to rotate shaft 110.

Figure 10:
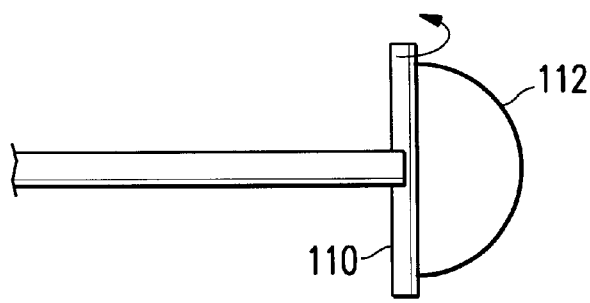
FIG. 10 is an illustration of a view of a second exemplary embodiment of second portions of a surgical tool in accordance with the present invention.
Figure 11:
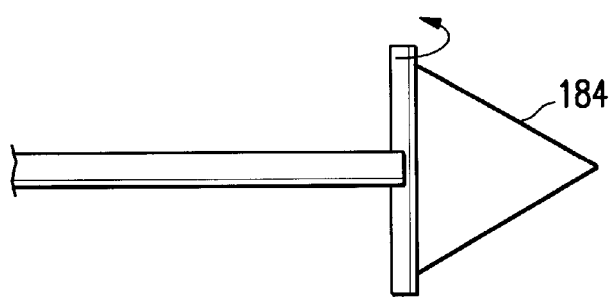
FIG. 11 is an illustration of a view of a third exemplary embodiment of second portions of a surgical tool in accordance with the present invention.
Figure 12:
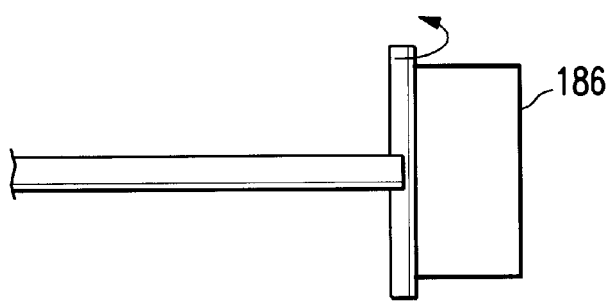
FIG. 12 is an illustration of a view of a fourth exemplary embodiment of second portions of a surgical tool in accordance with the present invention.
Figure 13:
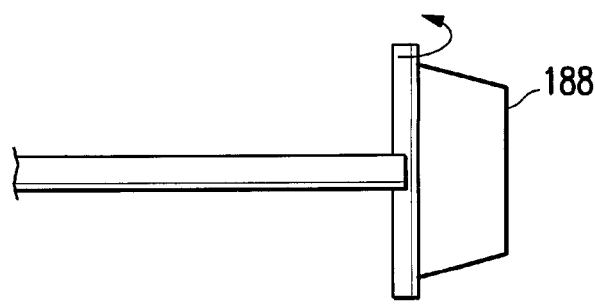
FIG. 13 is an illustration of a view of a fifth exemplary embodiment of second portions of a surgical tool in accordance with the present invention.
Figure 14:
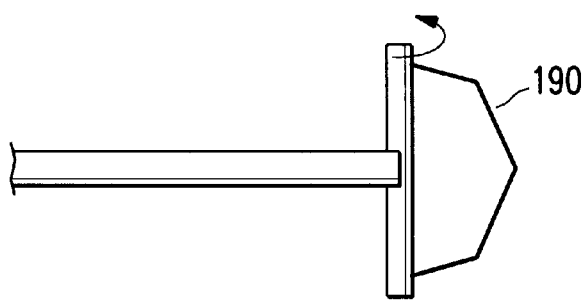
FIG. 14 is an illustration of a view of a sixth exemplary embodiment of second portions of a surgical tool in accordance with the present invention.

Turning now to FIGS. 10–21, numerous alternate embodiments of a cutting wire in accordance with the present invention are illustrated. FIG. 10 illustrates a cutting wire 112, as described above. Rotation of cutting wire 112 about the longitudinal axis of shaft 110 results in a hemispherical cut being made by the cutting wire. Alternative geometries for cutting wire 112 may also be used, such as a polygon. In the embodiment illustrated in FIG. 11, the polygon can be a triangle to form a triangular cutting wire 184. In the embodiment illustrated in FIG. 12, the polygon can be a rectangle, resulting in a rectangular cutting wire 186; cutting wires can be formed as other polygons, resulting in cutting wires 188 and 190, as will be readily appreciated by one of ordinary skill in the art.

Figure 15:
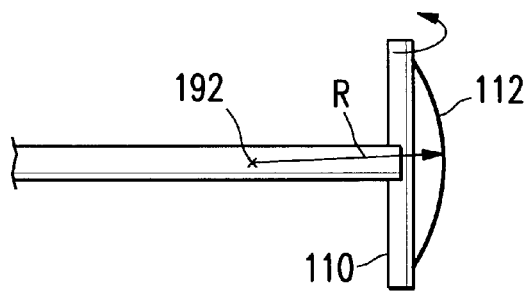
FIG. 15 is an illustration of a view of a seventh exemplary embodiment of second portions of a surgical tool in accordance with the present invention.
Figure 16:
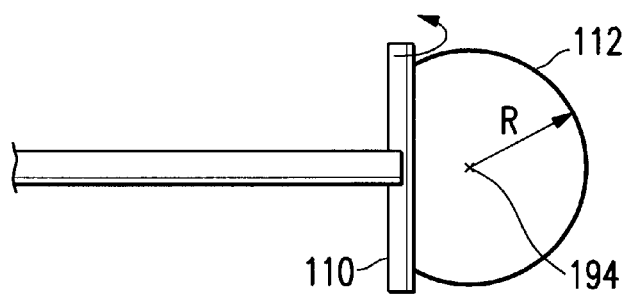
FIG. 16 is an illustration of a view of an eighth exemplary embodiment of second portions of a surgical tool in accordance with the present invention.
Figure 17:
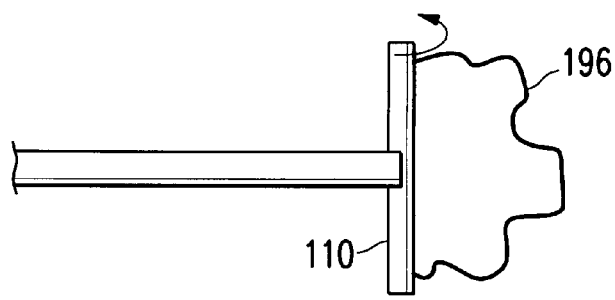
FIG. 17 is an illustration of a view of a ninth exemplary embodiment of second portions of a surgical tool in accordance with the present invention.
Figure 18:
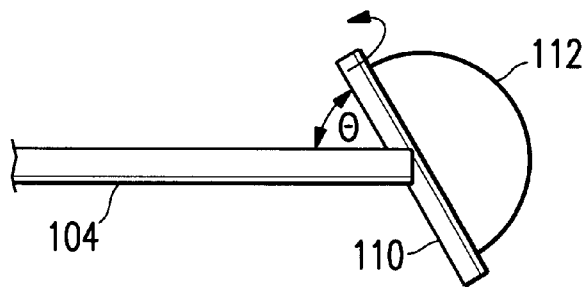
FIG. 18 is an illustration of a view of a tenth exemplary embodiment of second portions of a surgical tool in accordance with the present invention.

FIG. 15 illustrates that a cutting wire 112 can be formed as an arcuate loop which is described by a radius R taken from a point 192 proximally along probe 104 or cutting tip 106. Radius R can take essentially any value, and can be taken from a point 194 which is distal of the distal tip of tool 100, as illustrated in FIG. 16. The cutting wire can also take an irregular shape, as illustrated by wire 196 in FIG. 17.

Figure 19:
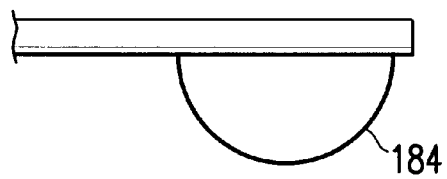
FIG. 19 is an illustration of a view of an eleventh exemplary embodiment of second portions of a surgical tool in accordance with the present invention.

Rotatable shaft 110, as described above, is perpendicular to the longitudinal axis of probe 104. In accordance with yet another embodiment of the present invention, shaft 110 is mounted to cutting tip 106 to form an included angle θ between the rotatable shaft and the probe or cutting tip. In general, angle θ can be any angle between 0 degrees and 90 degrees, i.e., $0° \geq \theta \geq 90°$. FIG. 19 illustrates an embodiment wherein angle θ is 0°, and there is no rotatable shaft 110. In the embodiment illustrated in FIG. 19, probe 104 or cutting tip 106 is rotated about its longitudinal axis in order to perform a cut.

Figure 20:
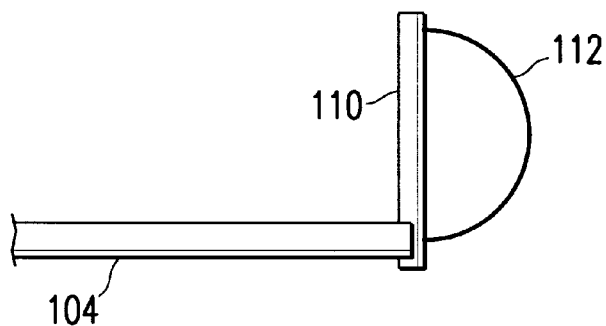
FIG. 20 is an illustration of a view of a twelfth exemplary embodiment of second portions of a surgical tool in accordance with the present invention.
Figure 21:
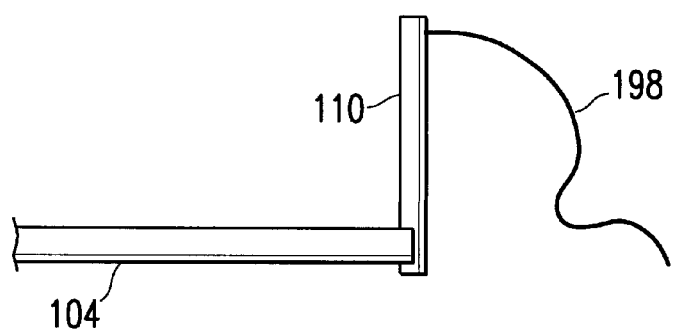
FIG. 21 is an illustration of a view of a thirteenth exemplary embodiment of second portions of a surgical tool in accordance with the present invention.

FIG. 20 illustrates yet another embodiment in accordance with the present invention, in which shaft 110 is asymmetrically mounted to probe 104. The embodiment illustrated in FIG. 20 can be useful for reaching under a tissue mass, e.g., the skin. The embodiment illustrated in FIG. 21 includes a cutting wire 198 which is not a loop, and therefore is formed of a relatively rigid material so that the cutting wire can be rotated within a tissue mass without significantly changing shape.

The operation of the apparatus in accordance with the present invention will now be described with reference being made to the drawing figures. A user of tool 100, e.g., a surgeon who is attempting to excise a tissue mass from a patient, forms an incision in the patient to access the tissue mass. The user locates the tissue mass and grasps handle 102. The user activates energy source 10 to supply electrical energy to cutting wire 112, which activation may be performed before, during, or after the user has pressed cutting wire 112 against tissue to be cut. Cutting wire 112 can also be inserted into the tissue mass, because of the electrical energy flowing through the cutting wire. When the user has properly located the cutting wire, the user rotates thumbwheel 108, which rotates the cutting wire around the tissue mass, thereby cutting the mass of tissue, including tissue opposite the surgical entry point. These steps can be repeated, as desired by the user, until the tissue mass has been completely cut, and is therefore ready for removal.

Shaped scalpels in accordance with the present invention can also be used as an adjunct to a standard surgical excision with a standard scalpel to help remove smooth contoured sections of tissue from the often ragged excision site walls.

While the invention has been described in detail with reference to preferred embodiments thereof, it will be apparent to one skilled in the art that various changes can be made, and equivalents employed, without departing from the scope of the invention.

What is claimed is:

1. A surgical tool comprising:
   a handle having a proximal end, a distal end, and a movable actuator;
   a probe having a longitudinal axis and which is attached to said handle distal end;
   a shaft which has a longitudinal axis and which is rotatably mounted to said probe at an angle with respect thereto;
   a motion transmission member connecting said movable actuator and said shaft;
   a cutting wire secured to said shaft, and
   an electrical conductor in electrical communication with said cutting wire extending proximally through said probe.

2. A surgical tool in accordance with claim 1, wherein said cutting wire forms a closed loop with said shaft.

3. A surgical tool in accordance with claim 1, wherein said movable actuator is a thumbwheel, and said motion transmission member is a push-and-pull wire which is looped around and secured to said shaft and secured to said thumbwheel.

4. A surgical tool in accordance with claim 3, wherein said thumbwheel comprises at least one arcuate block, said wire extends over said at least one arcuate block.

5. A surgical tool in accordance with claim 4, wherein said shaft further comprises two spaced apart ends and a bearing support between said ends, a channel being formed in said bearing support, said push-and-pull wire being attached to said shaft at said channel.

6. A surgical tool in accordance with claim 5, wherein said shaft comprises a pair of bearing supports and a rib extending between said bearing supports, said channel being formed in one of said pair of bearing supports.

7. A surgical tool in accordance with claim 6, wherein said rib forms a space between said bearing supports, said cutting wire includes two ends which extend through said shaft and into said space, and said electrical conductor further comprises an electrical connector in said space electrically connecting said cutting wire ends with said electrical conductor.

8. A surgical tool in accordance with claim 1, wherein said motion transmission member comprises a rotatable shaft having a beveled gear, and said shaft includes a beveled gear which meshes which said shaft beveled gear.

9. A surgical tool in accordance with claim 1, wherein said motion transmission member comprises a rotatable shaft having a pinion, and said shaft includes a ring gear which meshes with said shaft pinion.

10. A surgical tool in accordance with claim 1, wherein said motion transmission member comprises a rotatable cable having a hooked distal end which is attached to and is coaxial with said shaft.

11. A surgical tool in accordance with claim 1, wherein said motion transmission member comprises a rack which is movable along said probe and includes teeth, and said shaft comprises a pinion which meshes with said rack teeth.

12. A surgical tool in accordance with claim 1, wherein said motion transmission member comprises a rigid pushrod, and said shaft includes a lever extending therefore, said pushrod being pivotally attached to said lever.

13. A surgical tool in accordance with claim 1, wherein said cutting wire forms a polygon.

14. A surgical tool in accordance with claim 1, wherein said cutting wire forms a loop having a radius R taken from a point along said probe.

15. A surgical tool in accordance with claim 1, wherein said cutting wire forms a loop having a radius R taken from a point distal of said probe distal end.

16. A surgical tool in accordance with claim 1, wherein said cutting wire is attached to said rotatable shaft at only one end of said wire.

17. A surgical tool in accordance with claim 1, wherein said shaft is rotatably mounted to said probe at an angle less than or equal to 90°.

18. A surgical tool in accordance with claim 1, wherein said shaft is asymmetrically mounted to said probe.

19. A process of cutting tissue in a patient, comprising the steps of:

supplying electrical energy to a cutting wire which is secured to a shaft which has a longitudinal axis, and which is rotatably mounted to a probe at an angle with respect thereto; and rotating said shaft about said shaft axis while supplying electrical energy to said cutting wire.

20. A process in accordance with claim 19, wherein said probe has a longitudinal axis, and said rotating step comprises rotating said shaft about said shaft axis, wherein said shaft axis forms an angle $\theta$ of up to about 90° with said probe longitudinal axis.

* * * * *